US009642683B2

(12) United States Patent
Shah

(10) Patent No.: US 9,642,683 B2
(45) Date of Patent: May 9, 2017

(54) DENTAL PROPHYLAXIS CUP FOR MIXING AT LEAST TWO MEDIA PRIOR TO DISPENSING

(71) Applicant: Kerr Corporation, Orange, CA (US)

(72) Inventor: Dhawal Y. Shah, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 37 days.

(21) Appl. No.: 14/673,725

(22) Filed: Mar. 30, 2015

(65) Prior Publication Data

US 2015/0272712 A1    Oct. 1, 2015

Related U.S. Application Data

(60) Provisional application No. 61/972,910, filed on Mar. 31, 2014.

(51) Int. Cl.
*A61C 17/00* (2006.01)
*A61C 1/12* (2006.01)
*A61C 19/06* (2006.01)

(52) U.S. Cl.
CPC .............. *A61C 17/005* (2013.01); *A61C 1/12* (2013.01); *A61C 19/066* (2013.01)

(58) Field of Classification Search
CPC .................................................. A61C 17/005
See application file for complete search history.

(56) References Cited

U.S. PATENT DOCUMENTS

| 5,360,339 A | 11/1994 | Rosenberg |
| 5,775,905 A * | 7/1998 | Weissenfluh ......... A61C 17/005 433/125 |
| 6,146,140 A | 11/2000 | Bailey |
| 6,440,396 B1 | 8/2002 | McLaughlin |

(Continued)

FOREIGN PATENT DOCUMENTS

| EP | 0433773 A1 | 6/1991 |
| KR | 20100131217 A | 12/2010 |

(Continued)

OTHER PUBLICATIONS

European Patent Office, Search Report and Opinion issued in corresponding EP Application No. 15162046.5 dated Aug. 11, 2015, 7 pp.

*Primary Examiner* — Michael Kahelin
(74) *Attorney, Agent, or Firm* — Wood Herron & Evans LLP

(57) ABSTRACT

Provided is prophylaxis cup for dentistry, comprising a first section storing a first medium, a second section storing a second medium, and one or more channels between the first section and the second section, wherein the first section, the second section and the one or more channels are adapted to allow the first medium and the second medium to be mixed, in response to a rotational movement of the prophylaxis cup. Provided also is a method for using prophylaxis cup in which the prophylaxis cup is positioned on a patient's tooth. A control is triggered to rotate the prophylaxis cup to cause a first medium stored in a first section of the prophylaxis cup to be mixed with a second medium stored in a second section of the prophylaxis cup. Provided further is a prophylaxis angle for dentistry, comprising a hand-piece, with the prophylaxis cup coupled to the hand-piece.

22 Claims, 16 Drawing Sheets

(56) References Cited

U.S. PATENT DOCUMENTS

| | | |
|---|---|---|
| 7,510,396 B2 | 3/2009 | Lee et al. |
| 7,762,813 B2 | 7/2010 | Seals et al. |
| 2008/0076091 A1 | 3/2008 | Moreschini |
| 2008/0160482 A1 | 7/2008 | Jensen |
| 2010/0035205 A1 | 2/2010 | Wang et al. |
| 2011/0045434 A1 | 2/2011 | Stadeker |
| 2013/0164710 A1 | 6/2013 | Montgomery |

FOREIGN PATENT DOCUMENTS

| | | |
|---|---|---|
| WO | 95/23560 | 9/1995 |
| WO | 2005004746 A1 | 1/2005 |
| WO | 2009/117650 | 9/2009 |

\* cited by examiner

DENTAL PROPHYLAXIS CUP FOR MIXING AT LEAST TWO MEDIA PRIOR TO DISPENSING

CROSS-REFERENCE TO RELATED APPLICATION

This application claims the benefit of U.S. Provisional Application No. 61/972,910, filed Mar. 31, 2014, which Provisional Application is incorporated by reference in its entirety.

FIELD

The disclosure relates to a dental prophylaxis cup for mixing at least two media prior to dispensing.

BACKGROUND

In the field of dentistry, a patient's teeth may be polished by a dental practitioner. Polishing may be performed by using a soft rubber cup filled with an abrasive agent that spins on the end of a hand-piece. The hand-piece and the soft rubber cup may together be referred to as a prophylaxis angle for the purposes of this disclosure. The abrasive agent may also be referred to as a prophylaxis (prophy) paste. The prophy paste is a gritty toothpaste-like material that is stored in the prophylaxis cup that is spun around on the teeth to make the teeth shiny and smooth. In certain situations, the prophy paste may include a pumice-based formula and may be available in a variety of grits from fine to extra-coarse.

Certain dental treatments first use a prophy paste (abrasive agent) for polishing the teeth. During the course of a dental treatment, the dental practitioner may switch out prophylaxis cups repeatedly to use prophy pastes of different grits for polishing the teeth.

Subsequent to polishing the teeth, a whitening agent may be applied on the teeth for whitening the teeth. In certain situations, the whitening agent may comprise carbamide peroxide, where the carbamide peroxide breaks down in the mouth to form hydrogen peroxide. In other situations hydrogen peroxide may be directly used as a whitening agent. Many other types of whitening agents may be used to whiten teeth. Activating agents that enhance the whitening effects of hydrogen peroxide in combination with natural enzymes have also been proposed. Additionally, the beneficial effects of chemical catalysts added to whitening agents have been demonstrated in clinical research in dentistry.

SUMMARY OF THE PREFERRED EMBODIMENTS

Provided is prophylaxis cup for dentistry, comprising a first section storing a first medium, a second section storing a second medium, and one or more channels between the first section and the second section, wherein the first section, the second section and the one or more channels are adapted to allow the first medium and the second medium to be mixed, in response to a rotational movement of the prophylaxis cup.

In certain embodiments, the first medium is a dental paste comprising an abrasive agent and a whitening agent, and the second medium is a catalyst that activates the whitening agent.

In further embodiments, the first section is located peripheral to the second section. The catalyst has a lower viscosity than the dental paste, and the rotational movement of the prophylaxis cup causes the catalyst to move outwards to mix with the dental paste, during a treatment of a patient's teeth.

In additional embodiments, better whitening of a patient's teeth is obtained when the dental paste and the catalyst are mixed immediately prior to a treatment of the patient's teeth in comparison to pre-mixing the dental paste and the catalyst substantially ahead of time of the treatment of the patient's teeth.

In certain embodiments, the first medium comprises a whitening agent, and the second medium comprises an abrasive agent and a catalyst.

In additional embodiments, the first medium and the second medium each comprise one or more of an abrasive agent, a whitening agent, and a catalyst, wherein the whitening agent and the catalyst are in different sections of the prophylaxis cup.

In yet additional embodiments, the first section is located on one side of the prophylaxis cup and the second section is located on another side of the prophylaxis cup.

In further embodiments, the prophylaxis cup further comprises additional sections that store the first medium.

In certain embodiments, centrifugal forces generated by the rotational motion move the second medium stored in the second section via the one or more channels to the first section that stores the first medium.

In additional embodiments, inner walls of the first section and the second section are flared outwards towards an end of the prophylaxis cup that is open and proximal to the patient's teeth to allow movement of at least the mixed first and second medium towards the patient's teeth.

In yet additional embodiments, walls of the first and the second section have grooves or ridges to allow movement of at least the mixed first and second medium towards the patient's teeth.

In further embodiments, the prophylaxis cup is used in a single step prophylaxis and whitening system.

In additional embodiments, the prophylaxis cup is coupled to a hand-piece.

In further embodiments, the one or more channels are towards an end of the prophylaxis cup that is placed in contact with a patient's tooth to allow mixing of the first medium to the second medium immediately prior to application on the patient's tooth.

Provided further is a prophylaxis angle for dentistry, comprising a hand-piece, and a prophylaxis cup coupled to the hand-piece, wherein the prophylaxis cup comprises a first section storing a first medium, a second section storing a second medium, and one or more channels between the first section and the second section, wherein the first section, the second section and the one or more channels are adapted to allow the first medium and the second medium to be mixed, in response to a rotational movement of the prophylaxis cup.

In further embodiments of the prophylaxis angle, the first medium is a dental paste comprising an abrasive agent and a whitening agent, and the second medium is a catalyst that activates the whitening agent. In additional embodiments of the prophylaxis angle, the first section is located peripheral to the second section and the catalyst has a lower viscosity than the dental paste. The rotational movement of the prophylaxis cup causes the catalyst to move outwards to mix with the dental paste, during a treatment of a patient's teeth.

In additional embodiments of the prophylaxis angle, better whitening of the patient's teeth is obtained when the dental paste and the catalyst are mixed immediately prior to a treatment of a patient's teeth in comparison to pre-mixing the dental paste and the catalyst substantially ahead of time of the treatment of the patient's teeth.

Provided also is a method for using prophylaxis cup in which the prophylaxis cup is positioned on a patient's tooth. A control is triggered to rotate the prophylaxis cup to cause a first medium stored in a first section of the prophylaxis cup to be mixed with a second medium stored in a second section of the prophylaxis cup.

In further embodiments of the method for using the prophylaxis cup, the first medium comprises a whitening agent, and the second medium comprises an abrasive agent and a catalyst.

In additional embodiments of the method for using the prophylaxis cup, the first section is located peripheral to the second section and the catalyst has a lower viscosity than the dental paste. The rotational movement of the prophylaxis cup causes the catalyst to move outwards to mix with the dental paste, during a treatment of a patient's teeth.

In additional embodiments of the method for using the prophylaxis cup, better whitening of the patient's teeth is obtained when the dental paste and the catalyst are mixed immediately prior to a treatment of a patient's teeth in comparison to pre-mixing the dental paste and the catalyst substantially ahead of time of the treatment of the patient's teeth.

BRIEF DESCRIPTION OF THE DRAWINGS

Referring now to the drawings in which like reference numbers represent corresponding parts throughout.

DETAILED DESCRIPTION

In the following description, reference is made to the accompanying drawings which form a part hereof and which illustrate several embodiments. It is understood that other embodiments may be utilized and structural and operational changes may be made.

Certain types of dental pastes may contain both an abrasive agent and a whitening agent. Such dental pastes may be used to both polish and whiten a patient's teeth during a dental procedure. Such dental pastes may need the application of a catalyst, in a liquid solution form, on the patient's teeth immediately prior to the application of the dental paste on the patient's teeth to activate the whitening agent. Application of the liquid solution that includes the catalyst increases the time the patient has to spend in the dental chair and the total time the dental practitioner spends with the patient.

The catalyst may not be pre-combined in advance with the whitening agent as it decreases the whitening efficacy and potentially the shelf life of the product. Therefore, certain types of whitening agents require the use of a catalyst that may have to be mixed with the whitening agent immediately prior to or during the dental procedure in order for the procedure to be effective.

Certain embodiments provide a prophylaxis system having a multi-chambered prophylaxis cup that allows mixing of at least two media, such as a catalyst, and a dental paste that comprises an abrasive agent and a whitening agent. Certain embodiments provide a method for delivering the catalyst to the dental paste comprising the abrasive agent and the whitening agent immediately prior to the contact of the dental paste on the tooth surface to both polish and whiten the tooth.

Exemplary Embodiments

Figure 1:
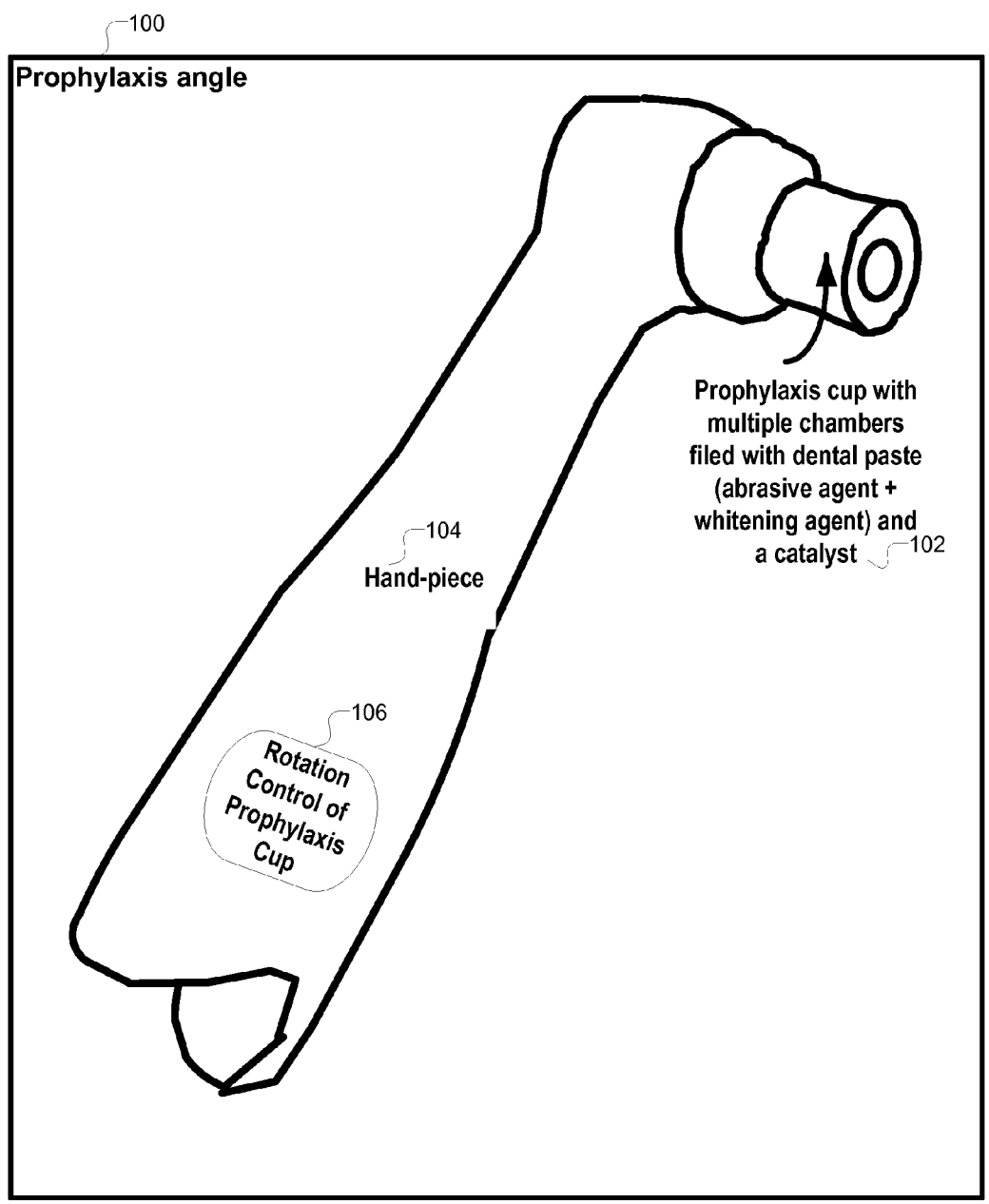
FIG. 1 illustrates a block diagram of a prophylaxis angle and an attached prophylaxis cup with multiple chambers filled with dental paste and a catalyst, in accordance with certain embodiments.

FIG. 1 illustrates a block diagram of a prophylaxis angle 100 and an attached prophylaxis cup 102 with multiple chambers filled with a dental paste and a catalyst, in accordance with certain embodiments. The dental paste is comprised of an abrasive agent and a whitening agent, where the whitening agent is activated by the catalyst.

The prophylaxis angle 100 has a hand-piece 104 used by dental practitioners to apply the dental paste that is activated by the catalyst for teeth polishing and whitening at the same time. The prophylaxis cup 102 is detachably or rigidly affixed to the distal tip of the hand-piece 104. The proximal end of the hand-piece 104 includes a control that when triggered may cause the prophylaxis cup to rotate at one or more rotational speeds measured in rotations per minute (RPM). The rotation of the prophylaxis cup may also be caused via other mechanisms such as by depressing the prophylaxis cup on the patient's teeth, or via mechanisms that complete a circuit.

In certain embodiments, the prophylaxis cup 102 has multiple chambers. In at least one of the multiple chambers the dental paste is stored, and in at least another of the multiple chambers the catalyst is stored. In response to the prophylaxis cup 102 being rotated, the catalyst moves from its chamber to a chamber storing the dental paste. A chemical reaction is triggered leading to generation of free radicals that may be used to remove chromophores that cause staining on teeth.

In certain embodiments, better whitening of a patient's teeth is obtained when the dental paste and the catalyst are mixed immediately prior to a treatment of the patient's teeth in comparison to pre-mixing the dental paste and the catalyst substantially ahead of time of the treatment of the patient's teeth.

Figure 2:
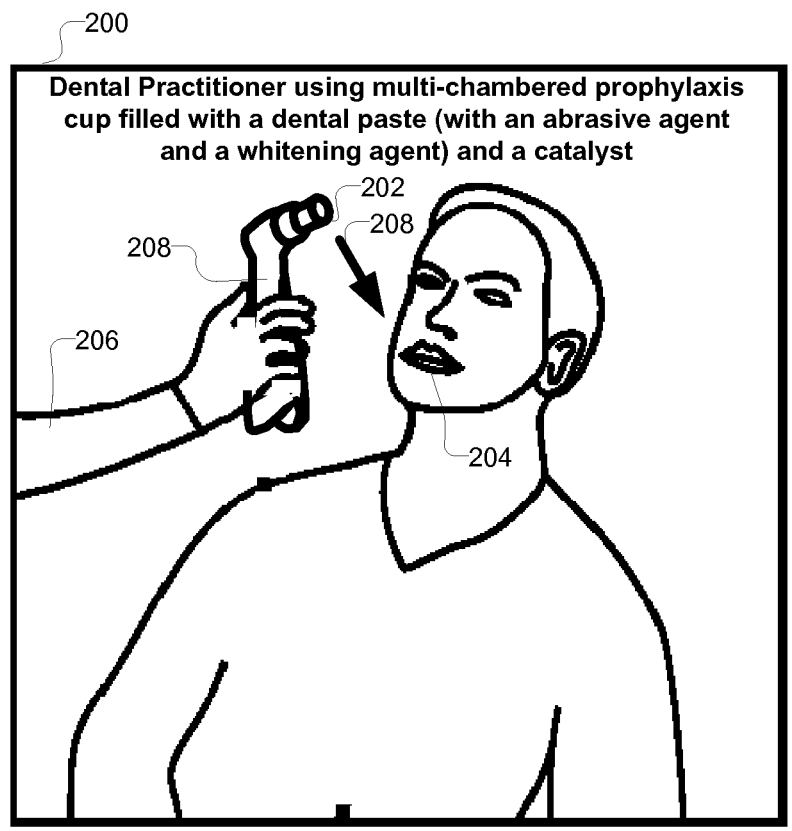
FIG. 2 illustrates a block diagram that shows exemplary positioning of a multi-chambered prophylaxis cup filled with dental paste and a catalyst on a patient's tooth, in accordance with certain embodiments.

FIG. 2 illustrates a block diagram 200 that shows exemplary positioning of a multi-chambered prophylaxis cup 202 filled with dental paste and a catalyst on a patient's tooth 204, in accordance with certain embodiments. The dental practitioner 206 holds the hand-piece 208 in his hand and places (shown via reference numeral 208) the multi-chambered prophylaxis cup 202 with the dental paste and the catalyst on a patient's tooth 204. Then the dental practitioner triggers the rotation of the prophylaxis cup 202 to start mixing the dental paste and the catalyst and the polishing and whitening of the tooth is initiated.

Figure 3:
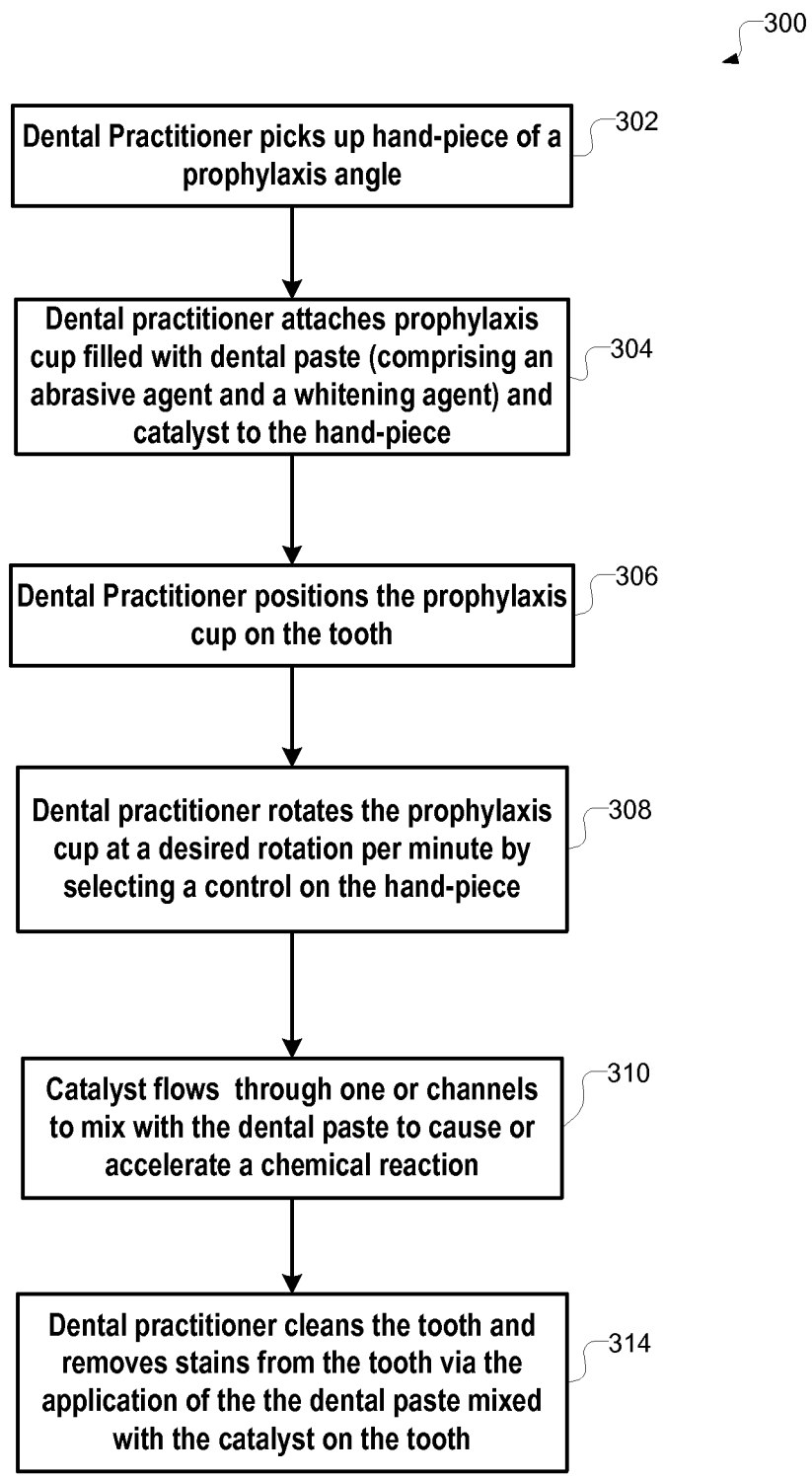
FIG. 3 illustrates a flowchart that shows operations performed by a dental practitioner in using a multi-chambered prophylaxis cup filled with dental paste and a catalyst on a patient's tooth, in accordance with certain embodiments.

FIG. 3 illustrates a flowchart 300 that shows operations performed by a dental practitioner to use a multi-chambered prophylaxis cup filled with dental paste and a catalyst on a patient's tooth, in accordance with certain embodiments.

Control starts at block 302 in which the dental practitioner picks up the hand-piece 104 of a prophylaxis angle 100. In certain embodiments, the dental practitioner attaches (at block 304) a prophylaxis cup 102 filled with dental paste and catalyst to the hand-piece. In other embodiments, the prophylaxis cup 102 is already filled and attached to the hand-piece of the prophylaxis angle.

Control proceeds to block 306, in which the dental practitioner positions the prophylaxis cup 102 on the tooth, and rotates (at block 308) the prophylaxis cup 102 at a desired rotation per minute by selecting a control 106 on the hand piece 104. In certain alternative embodiments, the operations shown in block 308 may be performed before the operations shown in block 306.

Catalyst stored in one of the chambers of the prophylaxis cup 102 flows (at block 310) through one or more channels to mix with the dental paste to cause or accelerate a chemical reaction. A channel may comprise an aperture, a hole, an opening or some other mechanism that may allow fluids, pastes, gels, liquids, etc., to pass through under certain conditions. The dental practitioner cleans the tooth and removes stains from the tooth via the application (at block 314) of the dental paste mixed with the catalyst on the tooth.

Therefore FIGS. 1-3 illustrate certain embodiments in which a multi-chambered prophylaxis cup is used to store the dental paste in one chamber and a catalyst in another chamber. Immediately prior to polishing and whitening a patient's tooth the catalyst is made to flow from its chamber to the chamber of the dental paste to cause or accelerate a chemical reaction that allows teeth to be both polished and whitened at the same time.

Many different types of multi-chambered prophylaxis cups may be used and certain exemplary embodiments are shown in FIGS. 4-12.

Figure 4:
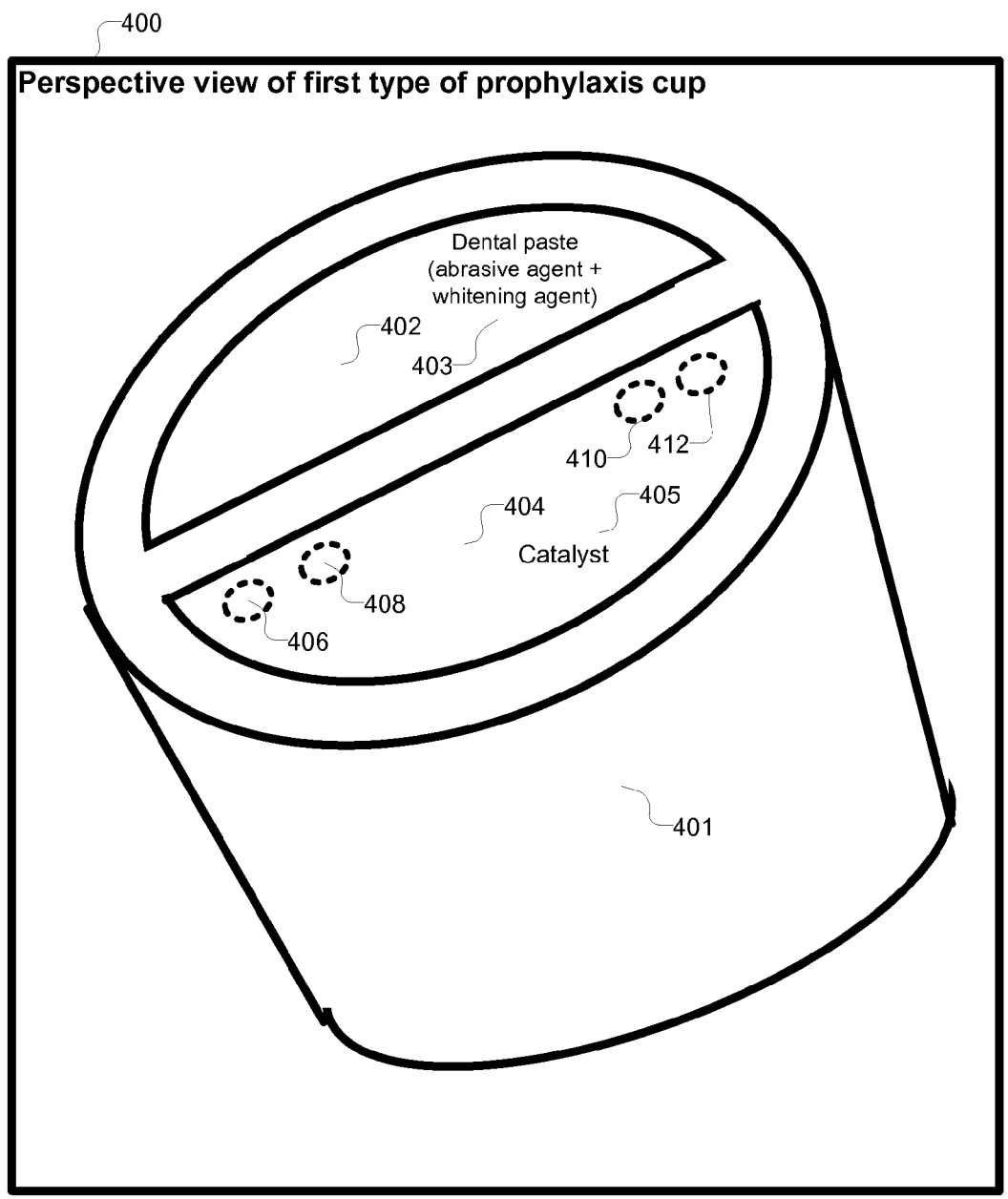
FIG. 4 illustrates a block diagram that shows a perspective view of a first type of prophylaxis cup, in accordance with certain embodiments.

FIG. 4 illustrates a block diagram 400 that shows a perspective view of a first type of prophylaxis cup 401, in accordance with certain embodiments. In the first type of prophylaxis cup there are two chambers 402, 404 with multiple channels 406, 408, 410, 412 connecting the two chambers.

In certain embodiments, chamber 402 stores the dental paste 403 and chamber 404 stores the catalyst 405 which has a lower viscosity than the dental paste 403. It should be noted that while the viscosity of the catalyst 405 is lower than that of dental paste 403, the viscosity of the catalyst 405 is high enough to prevent the catalyst 405 from dripping in large quantities on the patient's tooth directly from chamber 404.

When the prophylaxis cup 401 is rotated, the lower viscosity catalyst 405 passes through the channels 406, 408, 410, 412 into chamber 402 causing or accelerating a chemical reaction in chamber 402.

In certain embodiments, the walls of chamber 402 and chamber 404 have grooves or ridges to allow movement of the dental paste and catalyst towards the patient's teeth. In certain embodiments, the prophylaxis cup 401 is used as a single step prophylaxis and whitening system.

Figure 5:
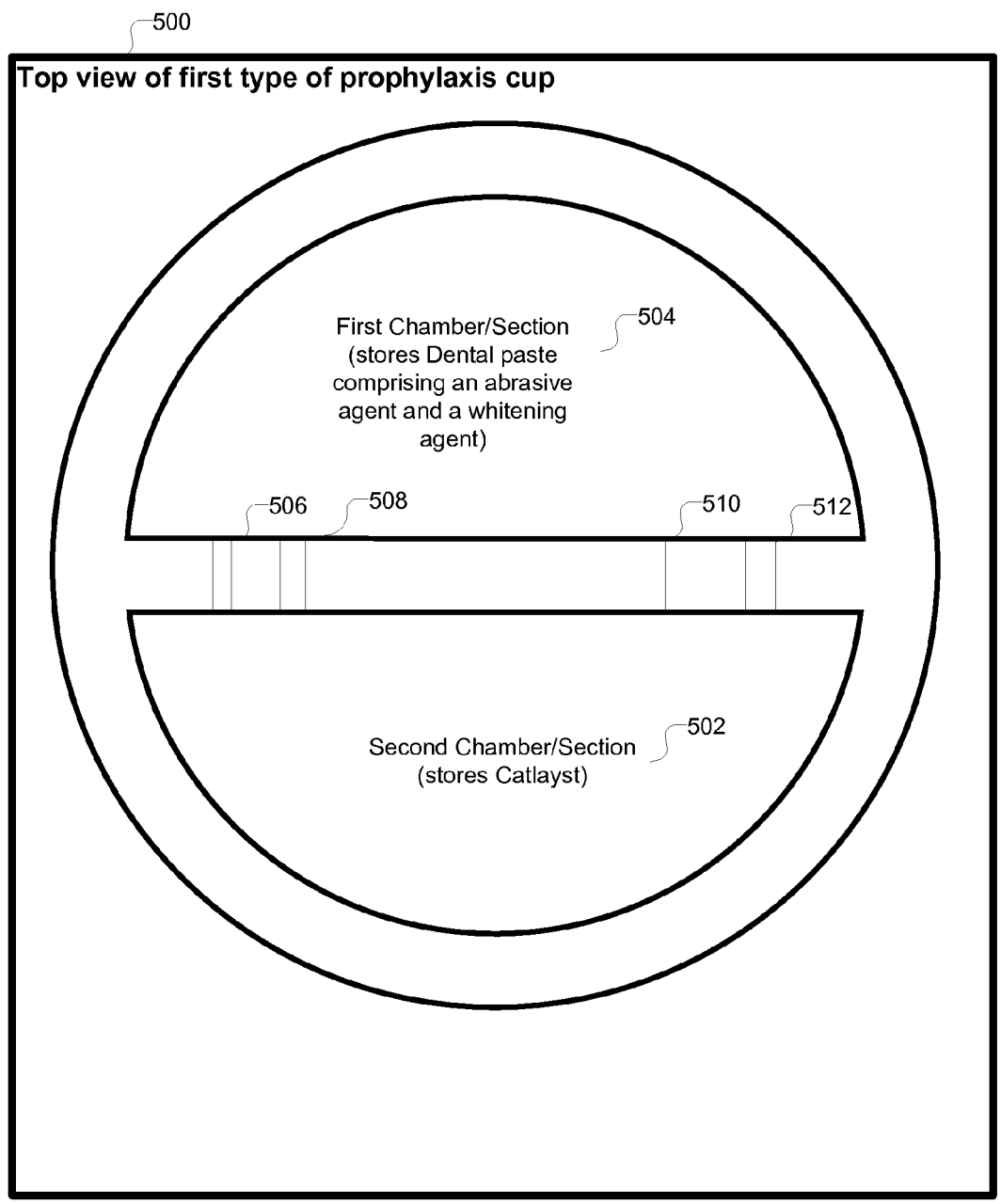
FIG. 5 illustrates a block diagram that shows a top view of the first type of prophylaxis cup, in accordance with certain embodiments.

FIG. 5 illustrates a block diagram 500 that shows a top view of the first type of prophylaxis cup 401, in accordance with certain embodiments. When the prophylaxis cup is rotated the lower viscosity catalyst stored in the second chamber 502 passes through the channels 506, 508, 510, 512 to the first chamber 504 causing or accelerating a chemical reaction in the first chamber 504 that stores the dental paste. In certain embodiments the chambers may be referred to as sections.

Figure 6:
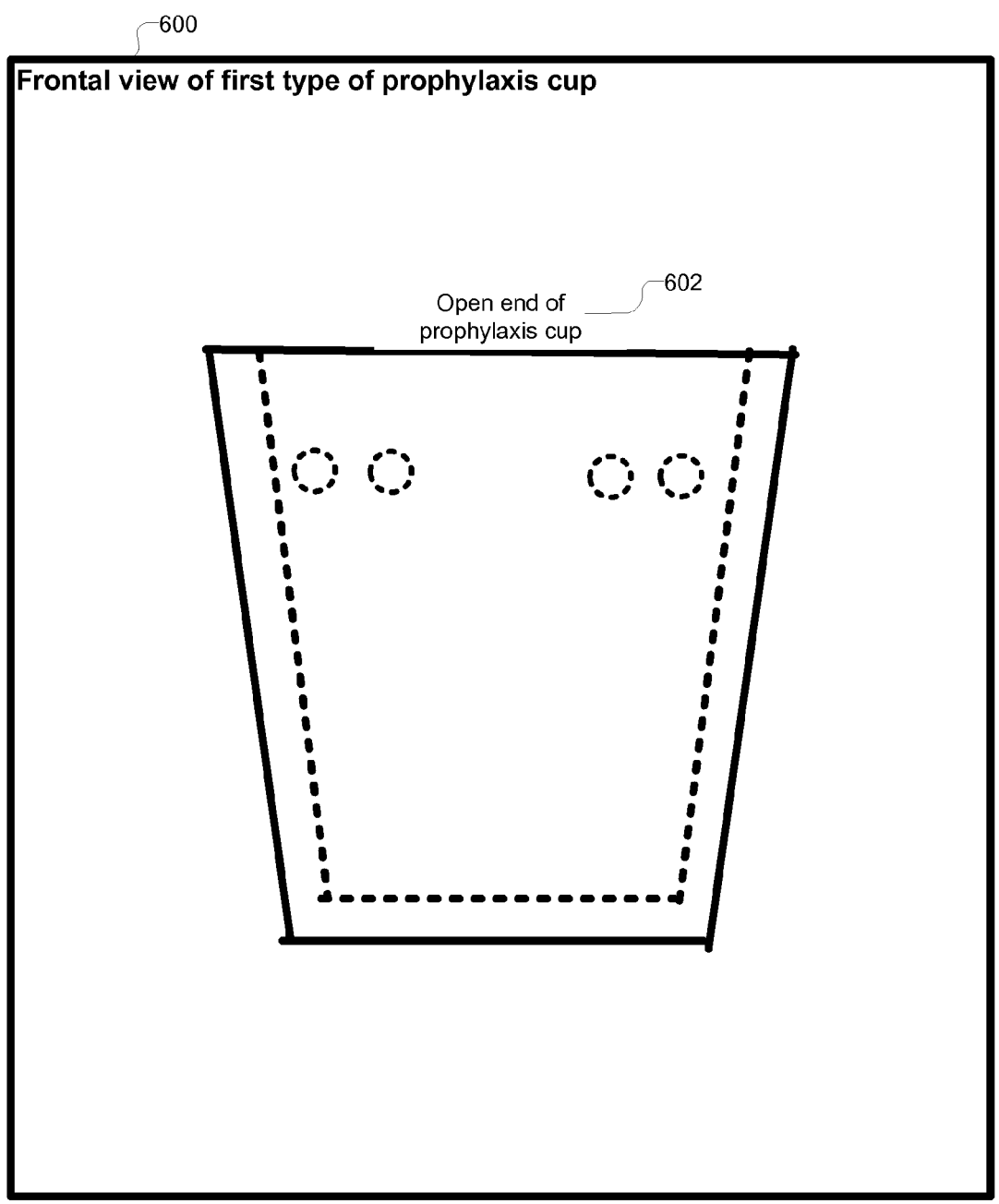
FIG. 6 illustrates a block diagram that shows a frontal view of the first type of prophylaxis cup, in accordance with certain embodiments.

FIG. 6 illustrates a block diagram 600 that shows a frontal view of the first type of prophylaxis cup 401, in accordance with certain embodiments. It may be seen that the inner walls of the first chamber and the second chamber are flared outwards towards the end of the prophylaxis cup that is open (shown via reference numeral 602) and proximal to the patient's teeth to allow movement of the mixed dental paste and catalyst towards the patient's teeth.

Figure 7:
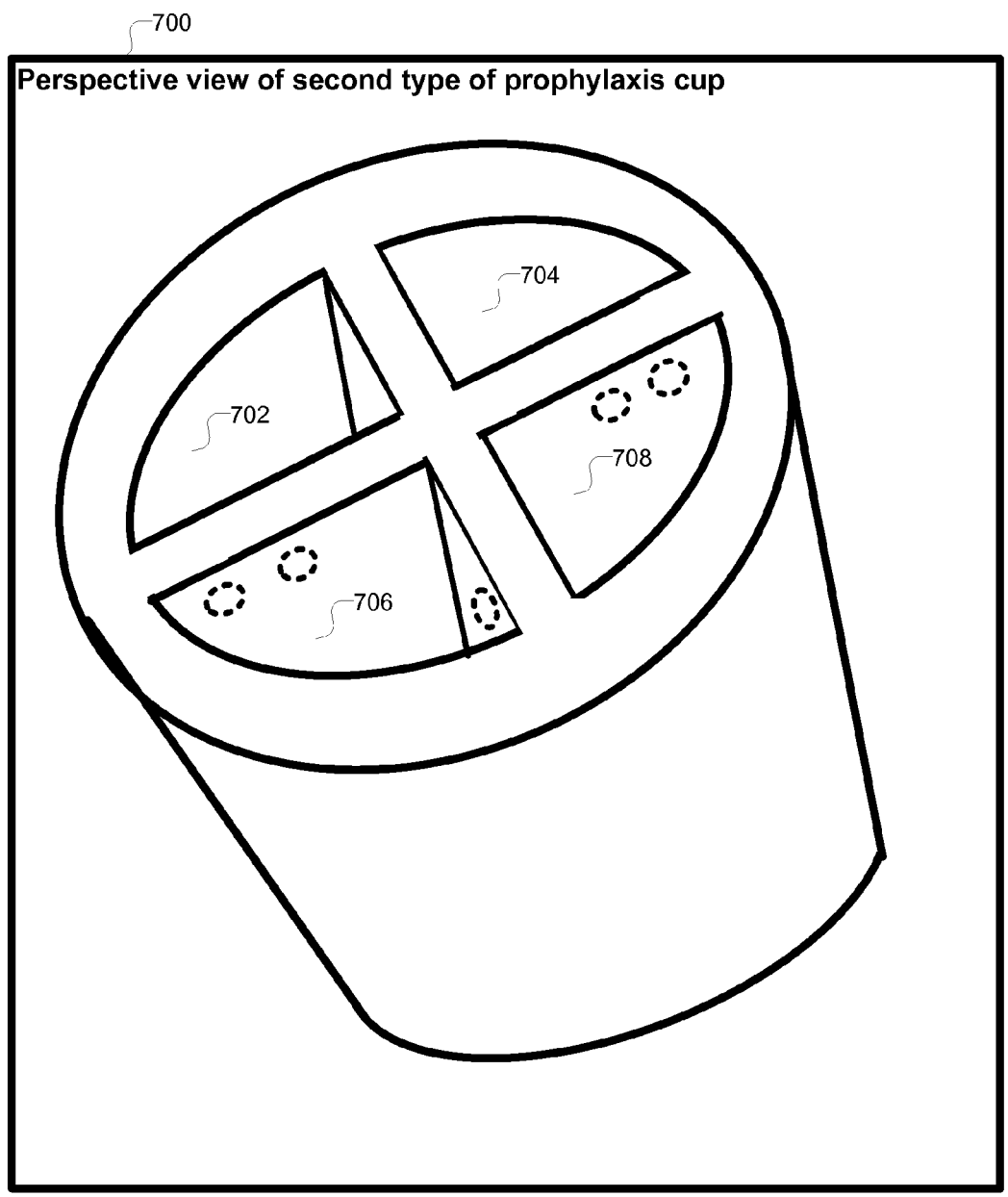
FIG. 7 illustrates a block diagram that shows a perspective view of a second type of prophylaxis cup, in accordance with certain embodiments.

FIG. 7 illustrates a block diagram 700 that shows a perspective view of a second type of prophylaxis cup, in accordance with certain embodiments. In the second type of prophylaxis cup there are four chambers 702, 704, 706, 708 with channels between the chambers. At least one of the four chambers store the catalyst while at least one or more of the other chambers store the dental paste.

Figure 8:
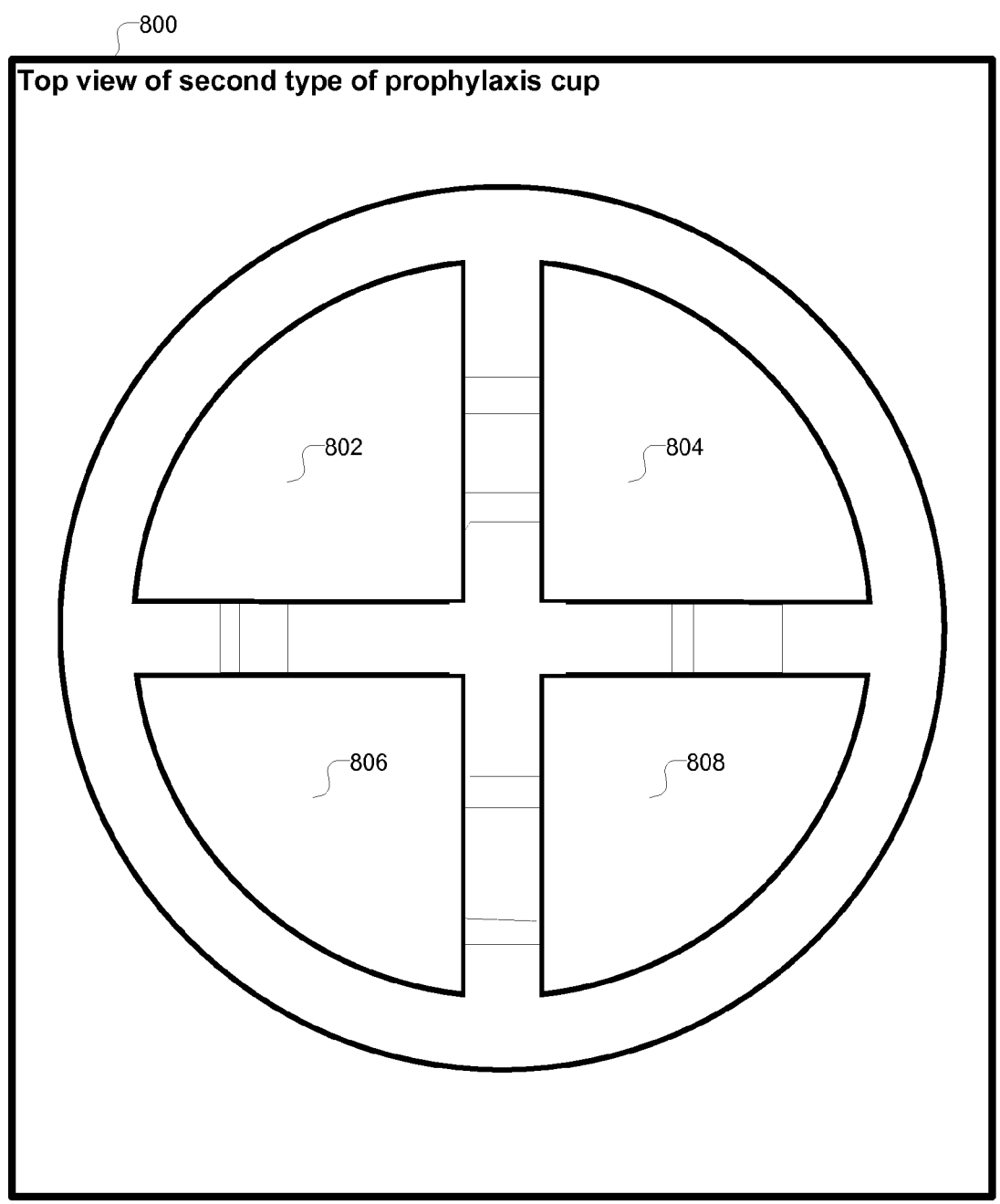
FIG. 8 illustrates a block diagram that shows a top view of the second type of prophylaxis cup, in accordance with certain embodiments.

FIG. 8 illustrates a block diagram 800 that shows a top view of the second type of prophylaxis cup, in accordance with certain embodiments. In the second type of prophylaxis cup there are four chambers 802, 804, 806, 808 with channels between the chambers. At least one of the four chambers store the catalyst while at least one or more of the other chambers store the dental paste.

Figure 9:
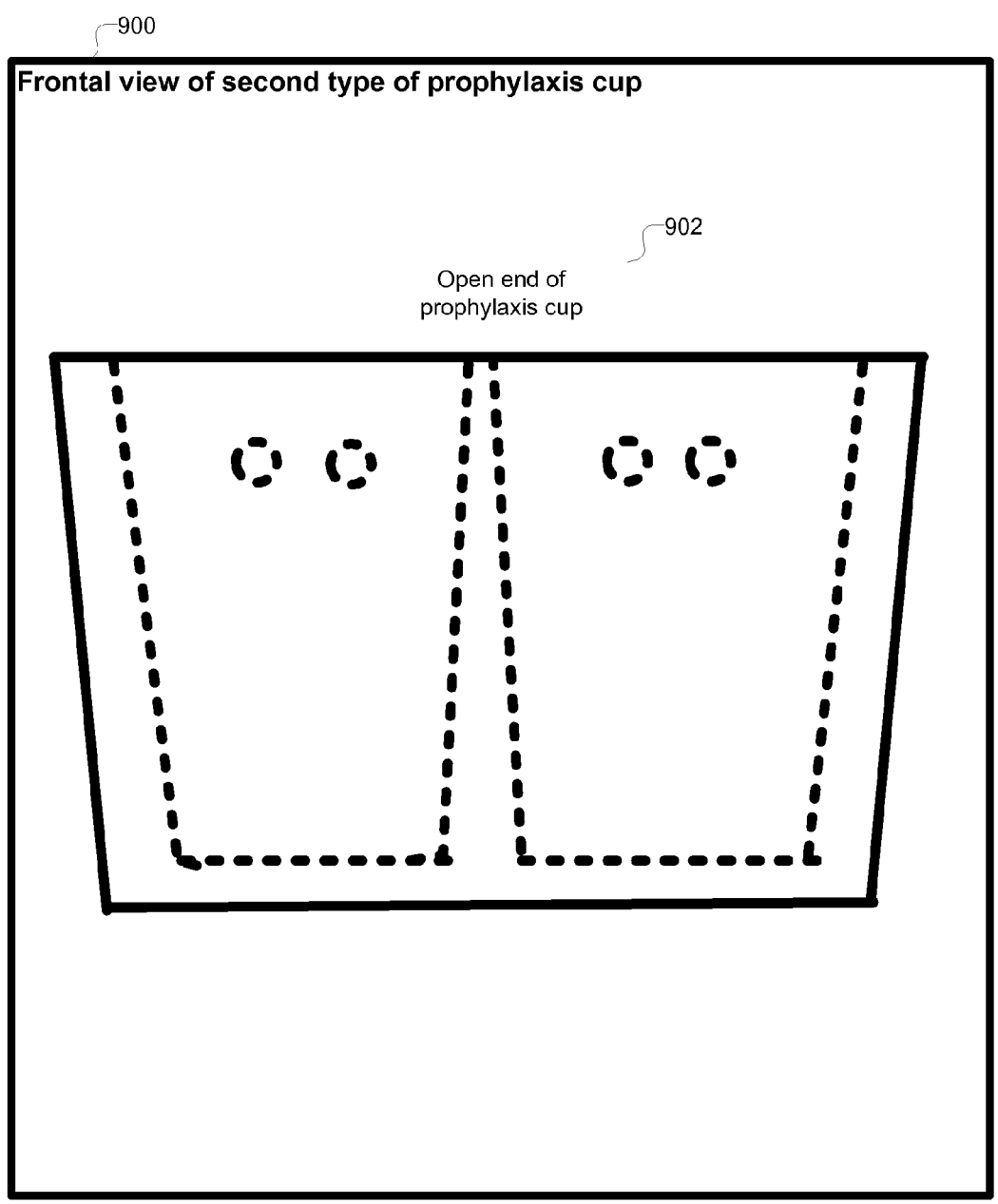
FIG. 9 illustrates a block diagram that shows a frontal view of the second type of prophylaxis cup, in accordance with certain embodiments.

FIG. 9 illustrates a block diagram 900 that shows a frontal view of the second type of prophylaxis cup, in accordance with certain embodiments. It may be seen that the inner walls of the chambers are flared outwards towards the end of the prophylaxis cup that is open (shown via reference numeral 902) and proximal to the patient's teeth to allow movement of the mixed dental paste and catalyst towards the patient's teeth.

Figure 10:
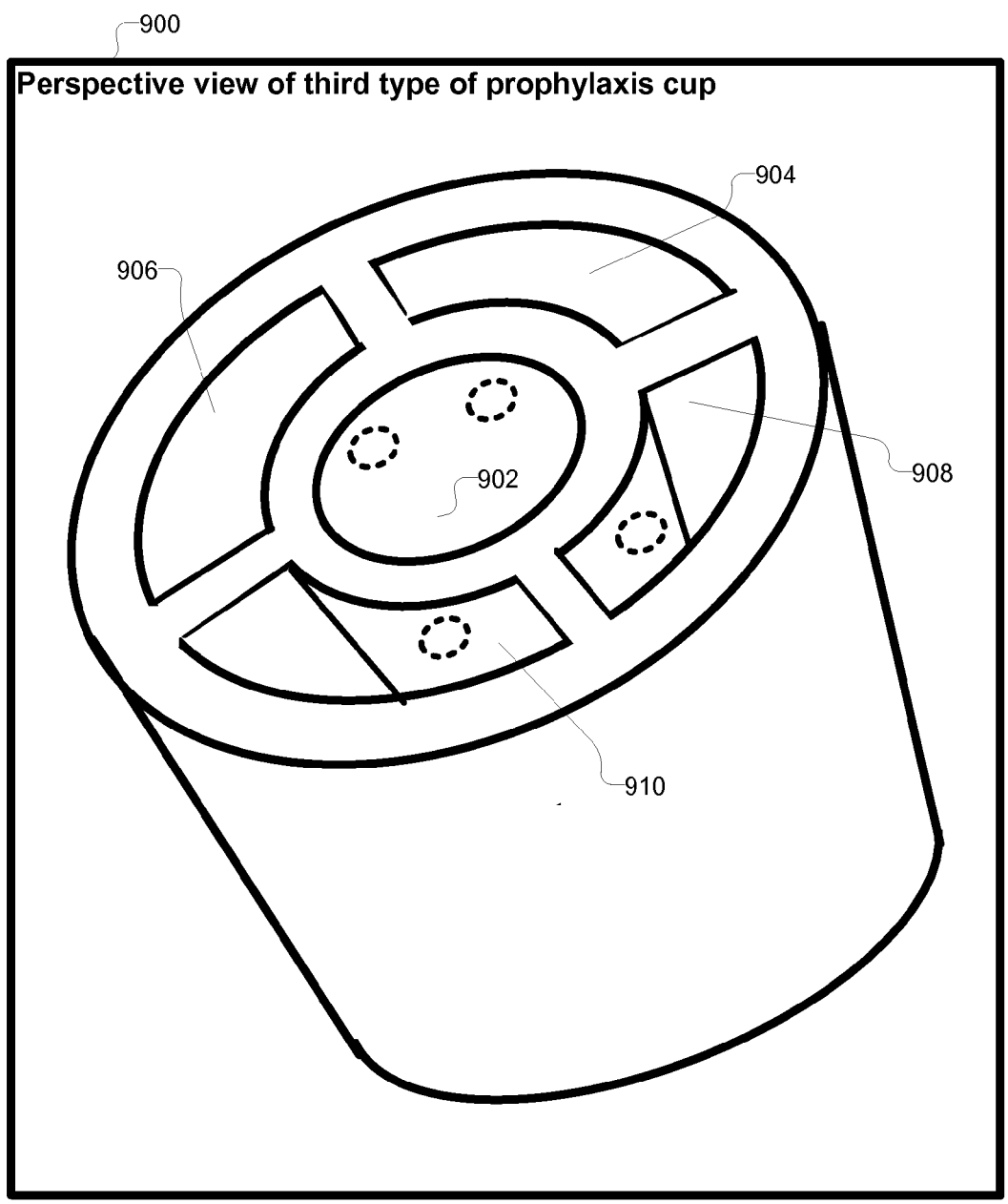
FIG. 10 illustrates a block diagram that shows a perspective view of a third type of prophylaxis cup, in accordance with certain embodiments.

FIG. 10 illustrates a block diagram 900 that shows a perspective view of a third type of prophylaxis cup, in accordance with certain embodiments. In the third type of prophylaxis cup there is a central chamber 902 that stores the catalyst. The other chambers 904, 906, 908, 910 store the dental paste. When the prophylaxis cup is rotated centrifugal forces move the less viscous catalyst from the central chamber 902 to the other chambers 904, 906, 908, 910 that store the dental paste, via the channels to generate or accelerate chemical reactions.

Figure 11:
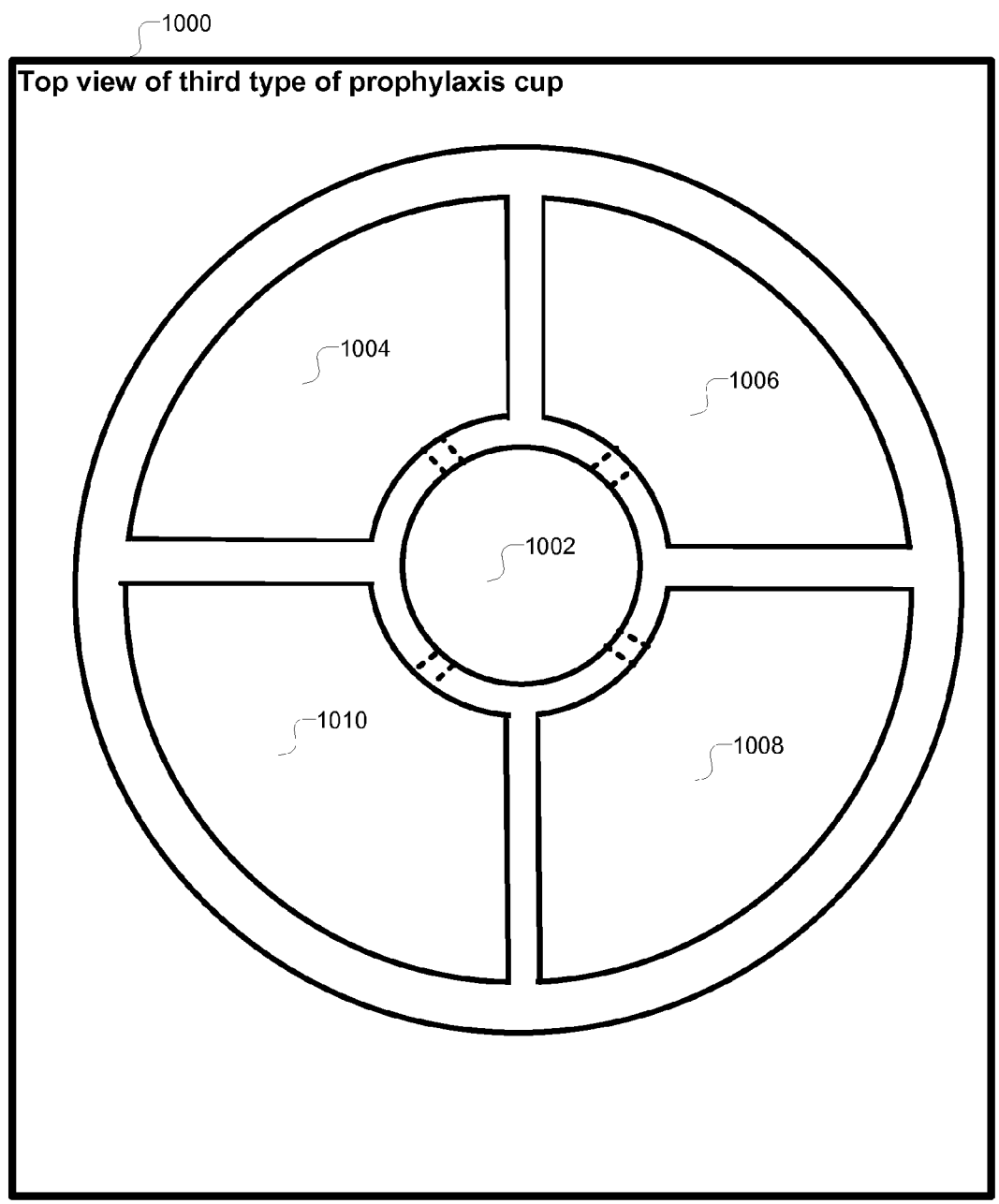
FIG. 11 illustrates a block diagram that shows a top view of the third type of prophylaxis cup, in accordance with certain embodiments.

FIG. 11 illustrates a block diagram 1000 that shows a top view of the third type of prophylaxis cup, in accordance with certain embodiments. In the third type of prophylaxis cup there is a central chamber 1002 that stores the catalyst. The other chambers 1004, 1006, 1008, 1010 store the dental paste. When the prophylaxis cup is rotated centrifugal forces move the less viscous catalyst from the central chamber 1002 to the other chambers 1004, 1006, 1008, 1010 that store the dental paste, via the channels, to generate or accelerate chemical reactions.

The dental paste removes stains by abrasion caused by the rotating prophylaxis cup. In order to achieve maximum abrasion, it may be beneficial to have the dental paste present at the peripheral chambers 1004, 1006, 1008, 1010 (as compared to being localized at the central chamber 1002) of the prophylaxis cup as shown in FIG. 11.

Figure 12:
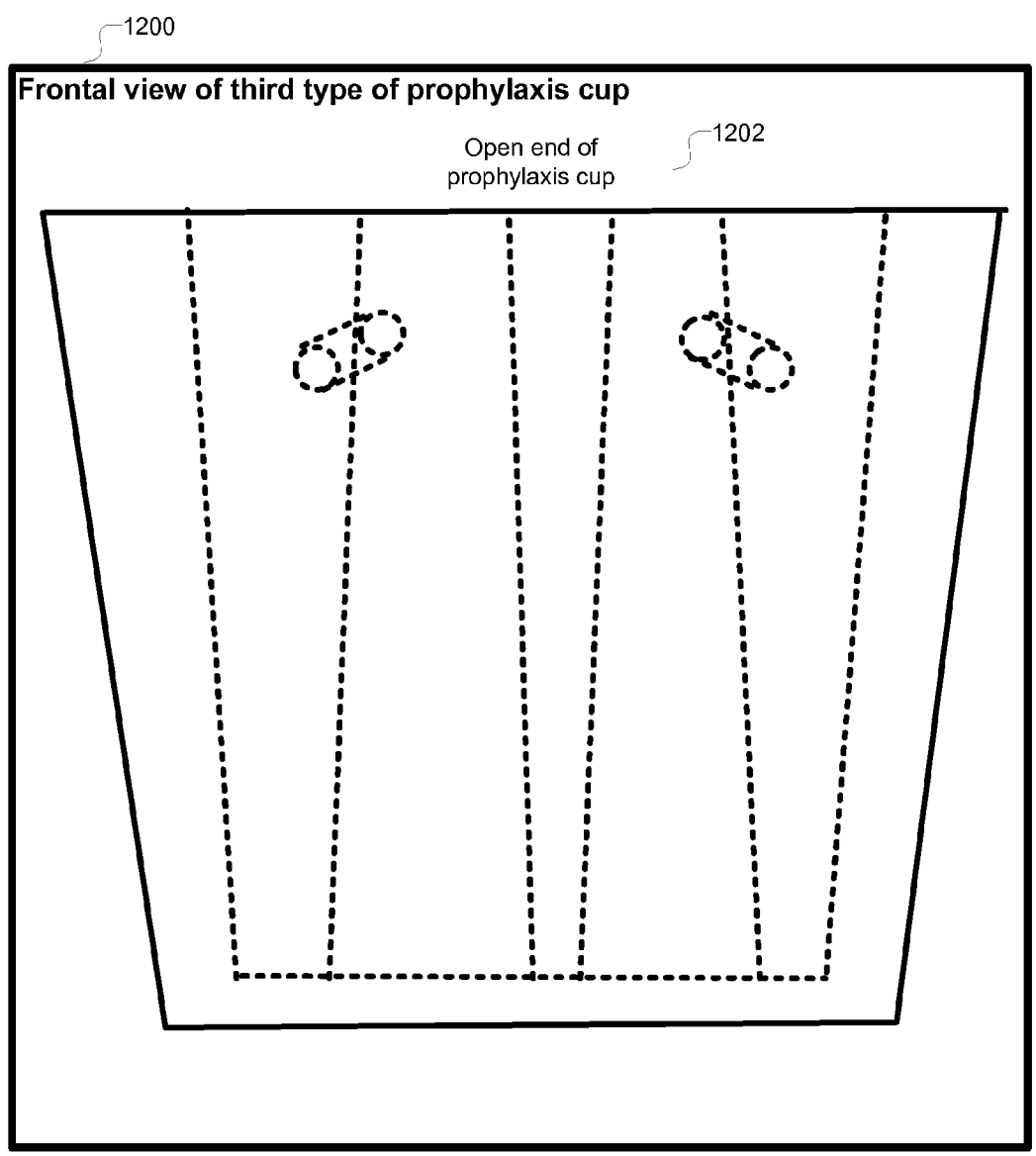
FIG. 12 illustrates a block diagram that shows a frontal view of the third type of prophylaxis cup, in accordance with certain embodiments.

FIG. 12 illustrates a block diagram 1200 that shows a frontal view of the third type of prophylaxis cup, in accordance with certain embodiments. It may be seen that the inner walls of the chambers are flared outwards towards the end of the prophylaxis cup that is open (shown via reference numeral 1202) and proximal to the patient's teeth to allow movement of the mixed dental paste and catalyst towards the patient's teeth.

Therefore, FIGS. 4-12 provide three different exemplary embodiments of prophylaxis cups. It is understood that other embodiments may be utilized and structural and operational changes may be made to the prophylaxis cups. For example, in certain embodiments, the walls forming the barrier between the catalyst chamber (i.e., the chamber containing the catalyst) and the prophylaxis chamber (i.e., the chamber containing the dental paste) may be of a flexible material such that the channels may expand to allow additional flow of the catalyst when the prophylaxis cup is rotated or depressed against the patient's tooth.

Figure 13:
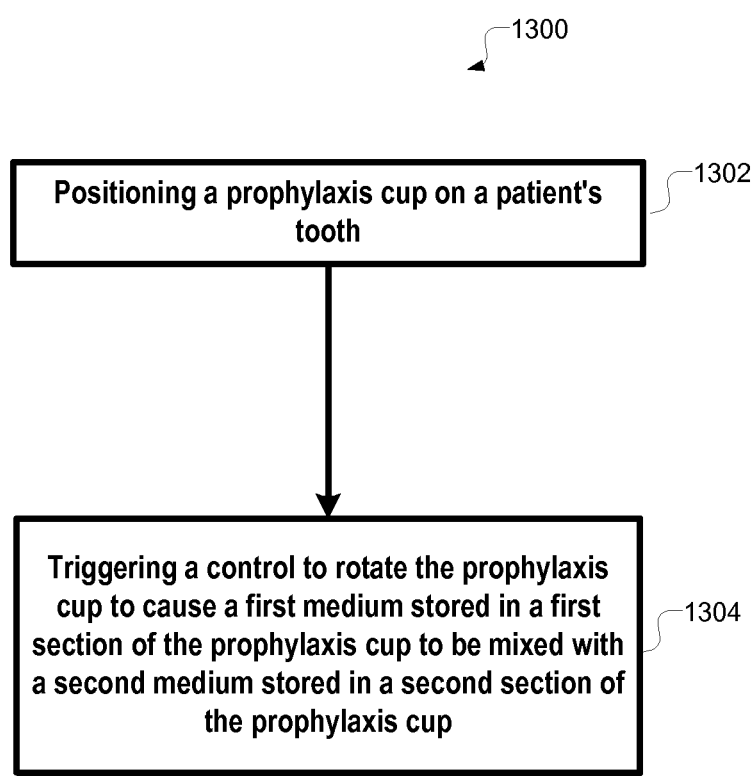
FIG. 13 illustrates a block diagram that show exemplary operations performed by a dental practitioner to use a multi-chambered prophylaxis cup, in accordance with certain embodiments.

FIG. 13 illustrates a block diagram 1300 that show exemplary operations performed by a dental practitioner to use a multi-chambered prophylaxis cup, in accordance with certain embodiments.

Control starts at block 1302 in which a prophylaxis cup is positioned on a patient's tooth. A control 106 is triggered to rotate the prophylaxis cup to cause a first medium (e.g., dental paste) stored in a first section (e.g., chamber) of the prophylaxis cup to be mixed with a second medium (e.g., a catalyst) stored in a second section (e.g., chamber) of the prophylaxis cup.

In additional embodiments, the first section is located peripheral to the second section (as shown in FIG. 10 where an exemplary first sections 906, 904, 908, 910 storing the dental paste are peripheral to the second section 902 that stores the catalyst), and the catalyst has a lower viscosity than the dental paste. The rotational movement of the prophylaxis cup causes the catalyst to move outwards to mix with the dental paste, during a treatment of a patient's teeth.

Figure 14:
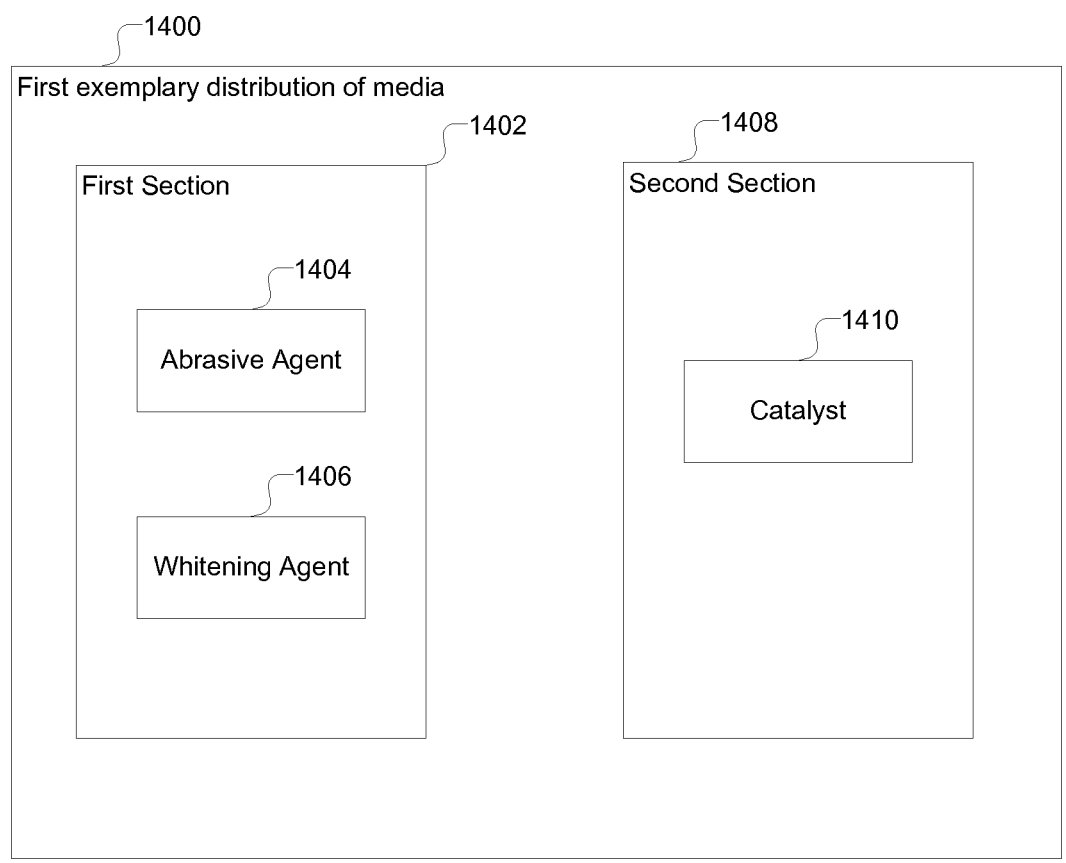
FIG. 14 illustrates a block diagram that show a first exemplary distribution of media in different sections of a prophylaxis cup, in accordance with certain embodiments.

FIG. 14 illustrates a block diagram 1400 that show a first exemplary distribution of media in different sections of a prophylaxis cup, in accordance with certain embodiments. In FIG. 14, the first section 1402 stores an abrasive agent 1404 and a whitening agent 1406, and the second section 1408 stores a catalyst 1410 that activates the whitening agent 1406 when the catalyst 1410 mixes with the whitening agent 1406.

Figure 15:
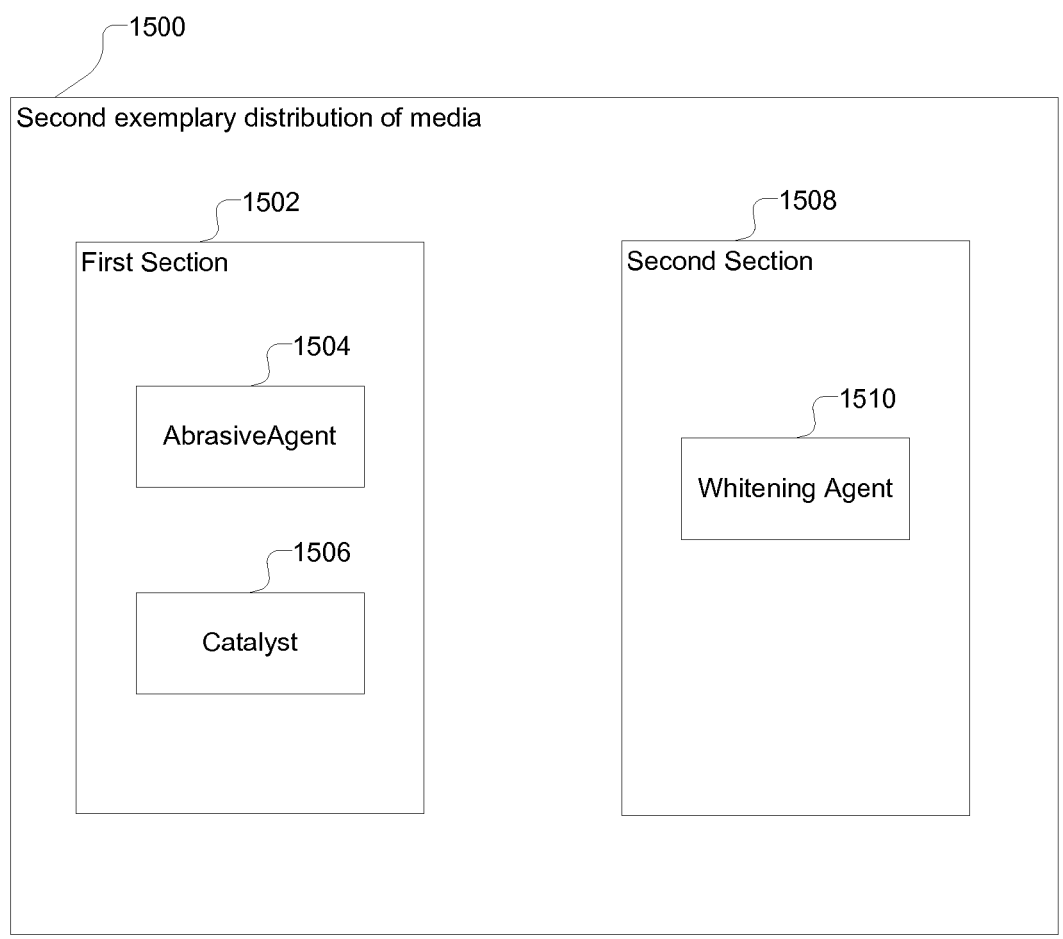
FIG. 15 illustrates a block diagram that show a second exemplary distribution of media in different sections of a prophylaxis cup, in accordance with certain embodiments.

FIG. 15 illustrates a block diagram 1500 that show a second exemplary distribution of media in different sections of a prophylaxis cup, in accordance with certain embodiments. In FIG. 15, the first section 1502 stores an abrasive agent 1504 and a catalyst 1506, and the second section 1508 stores a whitening agent 1510. When the catalyst 1506 mixes with the whitening agent 1510, the whitening agent 1510 is activated.

Figure 16:
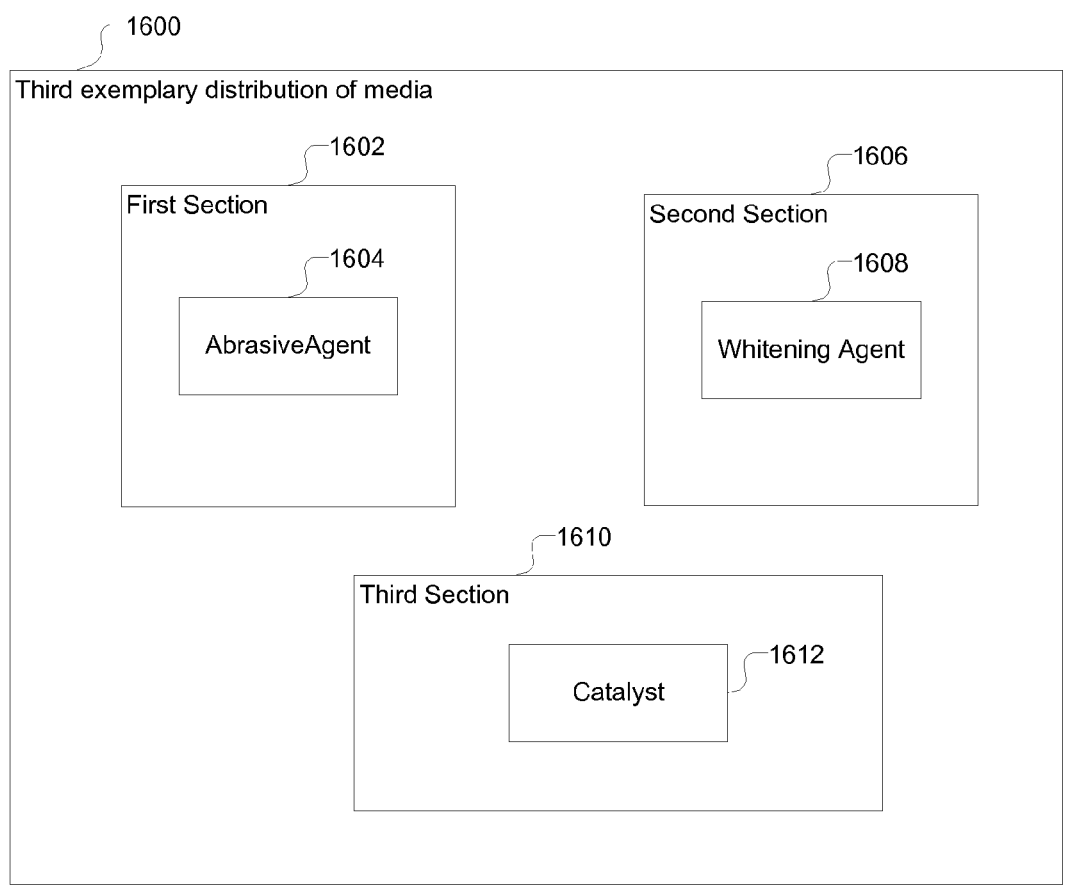
FIG. 16 illustrates a block diagram that show a third exemplary distribution of media in different sections of a prophylaxis cup, in accordance with certain embodiments.

FIG. 16 illustrates a block diagram 1600 that show a third exemplary distribution of media in different sections of a prophylaxis cup, in accordance with certain embodiments. In FIG. 16 there may be three sections in the prophylaxis cup. A first section 1602 stores the abrasive agent 1604, a second section 1606 stores the whitening agent 1608, and a third section 1610 stores the catalyst 1612. When the catalyst 1612 mixes with the whitening agent 1608 the whitening agent 1608 is activated. Other embodiments may distribute the media in differently. However, no matter what the distribution of media, the whitening agent and the catalyst are not allowed to be stored in the same chamber prior to rotation of the prophylaxis cup.

Therefore FIGS. 1-16 illustrate certain embodiments of a multi-chambered prophylaxis cup in which a catalyst is mixed with a dental paste comprising an abrasive agent and a whitening agent, immediately prior the application of the dental paste on the patient's tooth for polishing and whitening.

Additional Details of Embodiments

Aspects of the present invention are described below with reference to flowchart illustrations and/or block diagrams of methods or systems according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A prophylaxis cup for dentistry, comprising:
a first section storing a first medium;
a second section storing a second medium; and
one or more channels between the first section and the second section, wherein the first section, the second section and the one or more channels are adapted to allow the first medium and the second medium to be mixed, in response to a rotational movement of the prophylaxis cup, wherein the first and second mediums are each in the form of a paste or a liquid solution, one of the first and second mediums comprises a whitening agent, and the other of the first and second mediums comprises a catalyst that activates the whitening agent.

2. The prophylaxis cup of claim 1, wherein:
the first medium is a dental paste comprising an abrasive agent and the whitening agent; and
the second medium is a liquid solution of the catalyst that activates the whitening agent.

3. The prophylaxis cup of claim 2, wherein:
the first section is located peripheral to the second section;
the liquid solution of the catalyst has a lower viscosity than the dental paste; and
the rotational movement of the prophylaxis cup causes the liquid solution of the catalyst to move outwards to mix with at least one part of the dental paste, during a treatment of a patient's teeth.

4. The prophylaxis cup of claim 1, wherein:
the first medium comprises a liquid solution of the whitening agent; and
the second medium comprises a dental paste comprising an abrasive agent and the catalyst.

5. The prophylaxis cup of claim 1, wherein one or both of the first medium and the second medium comprise an abrasive agent.

6. The prophylaxis cup of claim 1, wherein the first section is located on one open side of the prophylaxis cup and the second section is located on another open side of the prophylaxis cup.

7. The prophylaxis cup of claim 1, further comprising: additional sections storing the first medium.

8. The prophylaxis cup of claim 1, wherein centrifugal forces generated by the rotational motion move the second medium stored in the second section via the one or more channels to the first section that stores the first medium.

9. The prophylaxis cup of claim 1, wherein inner walls of the first section and the second section are flared outwards towards an end of the prophylaxis cup that is open and proximal to the patient's teeth to allow movement of at least the mixed first and second medium towards the patient's teeth.

10. The prophylaxis cup of claim 1, wherein walls of the first and the second section have grooves or ridges to allow movement of at least the mixed first and second medium towards the patient's teeth.

11. The prophylaxis cup of claim 1, wherein the prophylaxis cup is coupled to a hand-piece.

12. The prophylaxis cup of claim 1, wherein the one or more channels are towards an end of the prophylaxis cup that is placed in contact with a patient's tooth to allow mixing of the first medium to the second medium immediately prior to application on the patient's tooth.

13. A prophylaxis angle for dentistry, comprising:
a hand-piece; and
a prophylaxis cup coupled to the hand-piece, wherein the prophylaxis cup comprises:
a first section storing a first medium;
a second section storing a second medium; and
one or more channels between the first section and the second section, wherein the first section, the second section and the one or more channels are adapted to allow the first medium and the second medium to be mixed, in response to a rotational movement of the prophylaxis cup, wherein the first and second mediums are each in the form of a paste or a liquid solution, one of the first and second mediums comprises a whitening agent, and the other of the first and second mediums comprises a catalyst that activates the whitening agent.

14. The prophylaxis angle of claim 13, wherein:
the first medium is a dental paste comprising an abrasive agent and the whitening agent; and
the second medium is a liquid solution of the catalyst that activates the whitening agent.

15. The prophylaxis angle of claim 14, wherein:
the first section is located peripheral to the second section;
the liquid solution of the catalyst has a lower viscosity than the dental paste; and
the rotational movement of the prophylaxis cup causes the liquid solution of the catalyst to move outwards to mix with the dental paste, during a treatment of a patient's teeth.

16. A method for using a prophylaxis cup, the method comprising:
positioning the prophylaxis cup on a patient's tooth; and
triggering a control to rotate the prophylaxis cup to cause a first medium stored in a first section of the prophylaxis cup to be mixed with a second medium stored in a second section of the prophylaxis cup, wherein the first and second mediums are each in the form of a paste or a liquid solution, one of the first and second mediums comprises a whitening agent, and the other of the first and second mediums comprises a catalyst that activates the whitening agent.

17. The method of claim 16, wherein:
the first medium is a dental paste comprising an abrasive agent and the whitening agent; and the second medium is a liquid solution of the catalyst that activates the whitening agent.

18. The method of claim 17, wherein:
the first section is located peripheral to the second section;
the liquid solution of the catalyst has a lower viscosity than the dental paste; and
the rotational movement of the prophylaxis cup causes the liquid solution of the catalyst to move outwards via one or more channels to mix with the dental paste, during a treatment of a patient's teeth.

19. A prophylaxis cup for dentistry, comprising:
a first section storing a first flowable medium in the form of a paste or liquid solution;
a second section storing a second flowable medium in the form of a paste or liquid solution that is different than the first medium in both composition and viscosity; and
one or more channels between the first section and the second section, wherein the first section, the second section and the one or more channels allow one of the first or second flowable mediums to flow through the channel to be mixed with the other of the first or second flowable mediums, in response to a rotational movement of the prophylaxis cup.

20. The prophylaxis cup of claim 19, wherein one of the first and second flowable mediums comprises a whitening agent, the other of the first and second flowable mediums comprises a catalyst that activates the whitening agent, and one or both of the first and second flowable mediums comprises an abrasive agent.

21. The prophylaxis cup of claim 19, wherein:
the first section is located peripheral to the second section;
the second flowable medium has a lower viscosity than the first flowable medium; and
the rotational movement of the prophylaxis cup causes the second flowable medium to move outwards to mix with the first flowable medium, during a treatment of a patient's teeth.

22. The prophylaxis cup of claim 19, wherein the first section is located on one open side of the prophylaxis cup and the second section is located on another open side of the prophylaxis cup.

* * * * *